(12) United States Patent
Qiu (10) Patent No.: US 11,167,098 B2
(45) Date of Patent: Nov. 9, 2021

(54) ELECTRONIC CIGARETTE

(71) Applicant: Jiangsu Jwei Electronics Co., Ltd., Changzhou (CN)

(72) Inventor: Wei-Hua Qiu, ChangZhou (CN)

(73) Assignee: Jiangsu Jwei Electronics Co., Ltd., Changzhou (CN)

( * ) Notice: Subject to any disclaimer, the term of this patent is extended or adjusted under 35 U.S.C. 154(b) by 722 days.

(21) Appl. No.: 15/672,219

(22) Filed: Aug. 8, 2017

(65) Prior Publication Data

US 2017/0333651 A1    Nov. 23, 2017

Related U.S. Application Data

(63) Continuation-in-part of application No. PCT/CN2015/075362, filed on Mar. 30, 2015.

(30) Foreign Application Priority Data

Feb. 15, 2015 (CN) .................... 201510083911.X (51) Int. Cl.
*A24F 47/00* (2020.01)
*A61M 15/06* (2006.01)

(52) U.S. Cl.
CPC ............ *A61M 15/06* (2013.01); *A24F 47/00* (2013.01); *A24F 47/008* (2013.01)

(58) Field of Classification Search
CPC ........ A61M 15/06; A24F 47/00; A24F 47/008
USPC ...................................................... 131/273
See application file for complete search history.

(56) References Cited

U.S. PATENT DOCUMENTS

| 2012/0260926 | A1  | 10/2012 | Tu et al. |
| 2014/0196732 | A1  | 7/2014  | Liu |
| 2015/0173420 | A1* | 6/2015  | Shi ............. A24F 47/008 131/329 |
| 2015/0335072 | A1* | 11/2015 | Giller ......... F21V 33/0004 131/328 |
| 2016/0270446 | A1* | 9/2016  | Shenkal ....... A24F 47/008 |
| 2016/0374392 | A1* | 12/2016 | Liu ............. A61M 15/06 392/404 |
| 2017/0013882 | A1* | 1/2017  | Liu ............. A24F 47/008 |

FOREIGN PATENT DOCUMENTS

| CN | 203058295 U | 7/2013 |
| CN | 203087525 U | 7/2013 |
| CN | 203168034 U | 9/2013 |
| CN | 203182014 U | 9/2013 |
| CN | 103355745 A | 10/2013 |

(Continued)

*Primary Examiner* — Michael J Felton
*Assistant Examiner* — Rashid A Alam
(74) *Attorney, Agent, or Firm* — ScienBiziP, P.C.

(57) ABSTRACT

A modular electronic cigarette which can be assembled into different shapes and configurations includes at least one atomization module and at least one battery module, the at least one atomization module and at least one battery module being detachably assembled together by means of magnetic connection, snap-fit, USB connection, or accessory to obtain various combination shapes of the electronic cigarette. Threaded connections between components are not required. The electronic cigarette can satisfy requirements of the user for simple and diverse combinations of components, thus increasing the user experience.

11 Claims, 8 Drawing Sheets

(56) References Cited

FOREIGN PATENT DOCUMENTS

| | | |
|---|---|---|
| CN | 203327954 U | 12/2013 |
| CN | 203435685 U | 2/2014 |
| CN | 203457810 U | 3/2014 |
| CN | 203676146 U | 7/2014 |
| CN | 204067467 U | 12/2014 |
| CN | 204070543 U | 1/2015 |
| CN | 204120231 U | 1/2015 |
| WO | 2014/146532 A1 | 9/2014 |
| WO | 2015/013967 A1 | 2/2015 |

* cited by examiner

ELECTRONIC CIGARETTE

CROSS-REFERENCE TO RELATED APPLICATIONS

The application is a continuation of International Application No. PCT/CN2015/075362 filed on Mar. 30, 2015, which claims priority to Chinese Patent Application No. 201510083911.X filed on Feb. 15, 2015, both of which are incorporated herein by reference in their entireties.

FIELD

The subject matter relates to electronic cigarettes, and more particularly, to an electronic cigarette which can be quickly assembled with diverse combinations.

BACKGROUND

Electronic cigarettes, also known as virtual cigarettes, electronic nebulizers, electronic cigars, have the same physical appearance and similar taste as conventional cigarettes, and are mainly used to simulate smoking.

Currently, an electronic cigarette in the market mainly includes an atomizer and a screw-in battery device connected to the atomizer, and the battery device includes a controller and batteries. The battery device can be either integral or split, but neither configuration is adequate. The controller and the batteries of the integral battery device are placed in the same battery case, and when one of the controller and the batteries fails, the entire battery device needs to be replaced. The split battery device on the market usually has a threaded connection, and because there is no uniform standard, different manufacturers produce different thread sizes, therefore limiting the component versatility of electronic cigarettes.

SUMMARY

A modular electronic cigarette is disclosed.

The electronic cigarette disclosed includes at least one atomization module and at least one battery module, the at least one atomization module and the at least one battery module being detachably assembled together by means of magnetic connection, snap-fit, USB connection, or accessory to obtain the electronic cigarette in various combination shapes.

In some embodiments, the electronic cigarette further includes a control module being detachably assembled together with the at least one atomization module and/or the at least one battery module.

In some embodiments, each atomization module and each battery module both comprise at least one magnetic member.

In some embodiments, each atomization module, each battery module and the control module all comprise at least one magnetic member.

In some embodiments, a housing of each atomization module and a housing of each battery module are both magnetic housings.

In some embodiments, the electronic cigarette further includes at least one ornament, the at least one magnetic member defines a mounting hole in which an electrical connection is accommodated, and the mounting hole defines a mounting groove for detachably assembling the ornament.

In some embodiments, at least one surface of each atomization module and at least one surface of each battery module are both provided with a joint or a connection groove, and the at least one atomization module and the at least one battery module are detachably connected together by means of snap-fit manner.

In some embodiments, at least one surface of each atomization module, at least one surface of each battery module and at least one surface of the control module are all provided with a joint or a connection groove, and the at least one atomization module, the at least one battery, and the control module are detachably connected together by means of snap-fit manner.

In some embodiments, the electronic cigarette includes an accessory, the at least one atomization module and the at least one battery module are detachably mounted on the accessory by magnetic attraction or snap-fit engagement.

In some embodiments, the electronic cigarette comprises an accessory, the at least one atomization module, the at least one battery module and the control module are detachably mounted on the accessory by magnetic attraction or snap fit engagement.

In some embodiments, the accessory includes a plurality of joints or connection slots, each atomization module and each battery module are both provided with a connection slot or a joint, and each atomization module and each battery module is slidably mounted to the accessory.

In some embodiments, a configuration and/or shape of the accessory is selected depending on the component combination of the electronic cigarette.

In some embodiments, the number of the battery modules is two or more than two.

The electronic cigarette has different combinations of the atomization module, control module, and battery module, such that the electronic cigarette can satisfy requirements of the users for simple and diversified operation, thus increasing the user experience.

| ELEMENT LISTING | | | | |
|---|---|---|---|---|
| electronic cigarette | 100 | atomization module | 110 | first magnetic member | 111 |
| second magnetic member | 112 | first positive contact | 113 | second positive contact | 114 |
| atomization device | 115 | control module | 120 | third magnetic member | 121 |
| fourth magnetic member | 122 | third positive contact | 123 | fourth positive contact | 124 |
| fifth positive contact | 125 | sixth positive contact | 126 | controller assembly | 127 |
| battery module | 130 | fifth magnetic member | 131 | sixth magnetic member | 132 |
| seventh positive contact | 133 | eighth positive contact | 134 | Power supply battery | 135 |
| cigarette holder | 140 | elastic member | 150 | ornament | 160 |
| sleeve | 170 | insulating member | 180 | mounting hole | 190 |
| first end surface | 11a | first side surface | 11b | second end surface | 12a |
| second side surface | 12b | third side surface | 12c | third end surface | 13a |
| fourth side surface | 13b | electronic cigarette | 200 | atomization module | 210 |
| control module | 220 | battery module | 230 | joint | 240 |
| connection groove | 250 | ornament plate | 260 | electronic cigarette | 300 |
| atomization module | 310 | control module | 320 | battery module | 330 |
| accessory | 340 | locking portion | 360 | slot | 380 |

DETAILED DESCRIPTION

The present disclosure will become more apparent from the following detailed description taken in conjunction with the accompanying drawings. A number of specific details are set forth in the following description to facilitate a thorough understanding of the present disclosure. It is to be understood that the invention may be practiced otherwise than as specifically described herein without departing from the spirit and scope of the invention, and that the invention is not limited to the specific embodiments disclosed below.

It should be noted that when the element is referred to as being "fixed to" another element, it may be directly attached on another element or there may also be a centered element. When an element is considered to be "connected" to another element, it can be directly connected to another component or may also have a centered element.

Unless otherwise defined, all technical and scientific terms used herein have the same meaning as commonly understood by one of ordinary skill in the art to which this invention pertains. The terminology used herein in the specification of the present disclosure is for the purpose of describing particular embodiments only and is not intended to limit the invention. The term "and/or" as used herein includes any and all combinations of one or more of the associated listed items.

The First Embodiment

Figure 1:
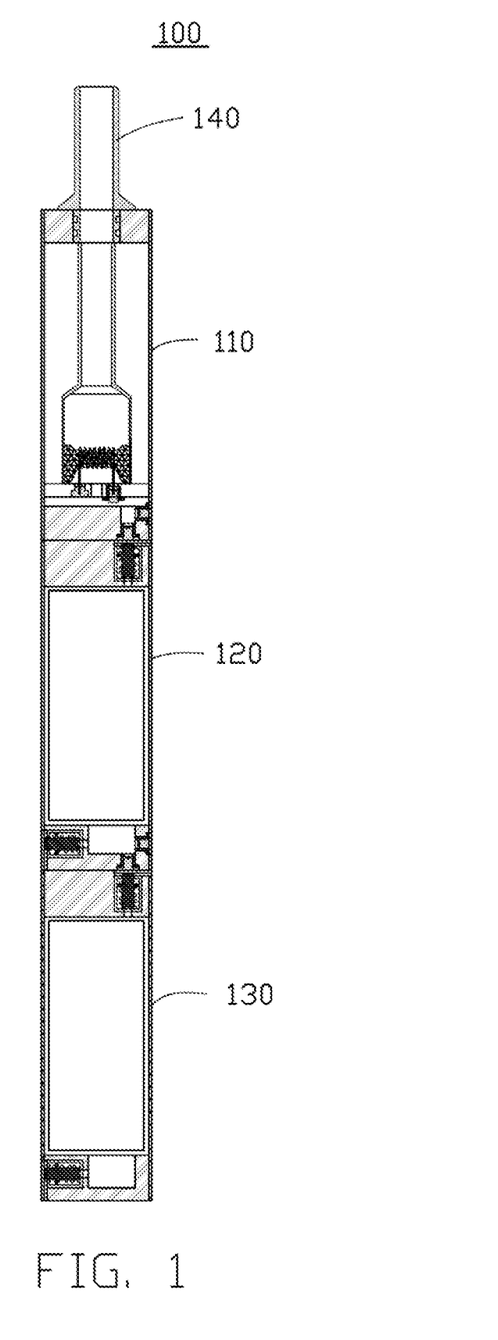
FIG. 1 is a schematic diagram of an electronic cigarette according to an embodiment of the present disclosure, wherein the electronic cigarette is assembled end to end.
Figure 2:
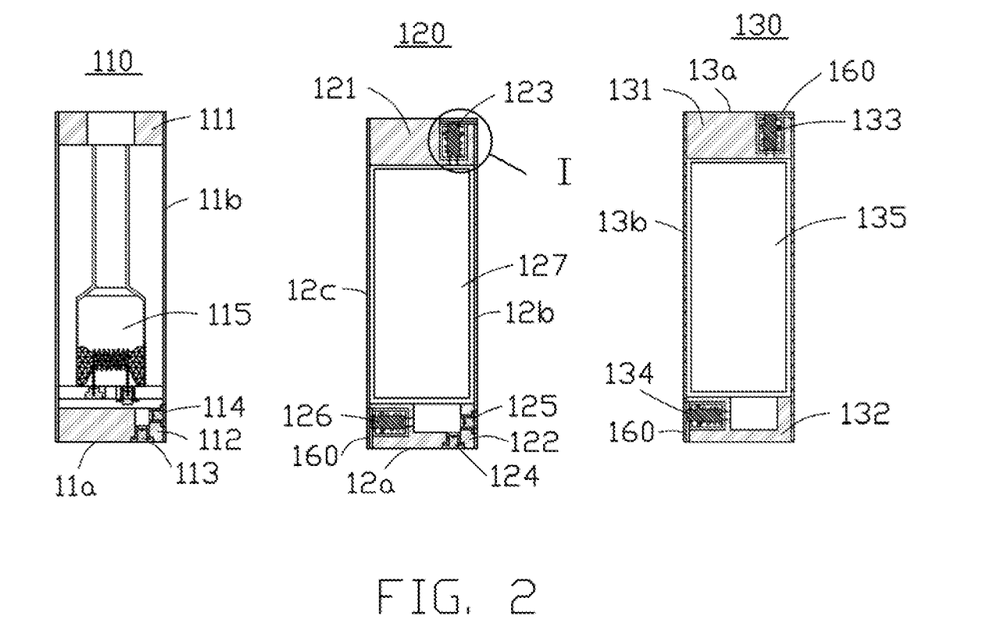
FIG. 2 is a schematic diagram of an atomization module, a control module, and a battery module of the electronic cigarette in FIG. 1.
Figure 3A:
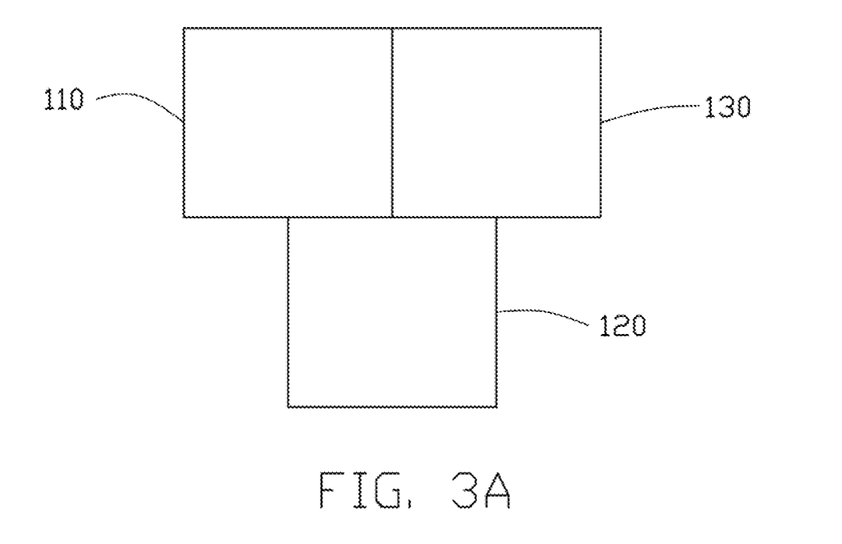
FIG. 3A is a schematic diagram of a connection of the atomization module, the control module, and the battery module of the electronic cigarette in FIG. 1 according an embodiment of the present disclosure.
Figure 3B:
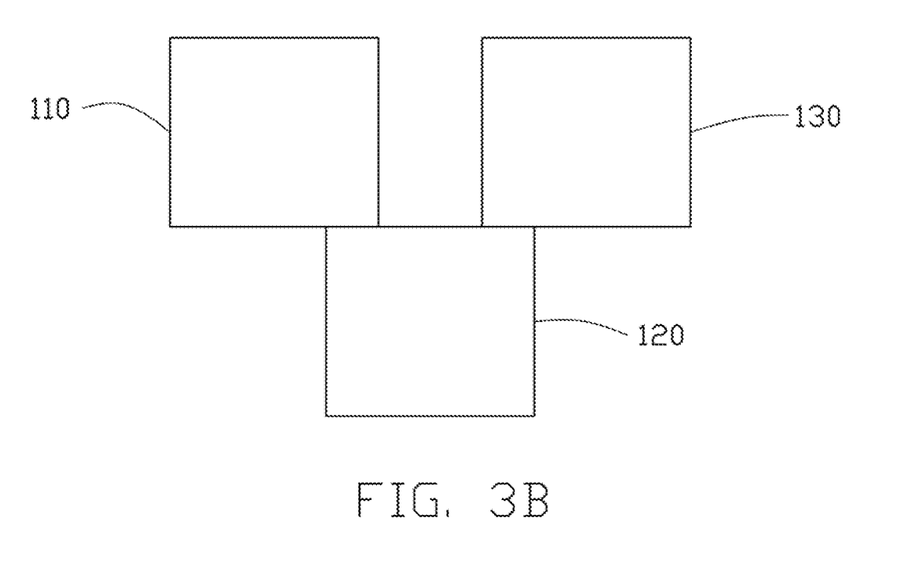
FIG. 3B is schematic diagram of a connection of the atomization module, the control module, and the battery module of the electronic cigarette in FIG. 1 according to another embodiment of the present disclosure.

Referring to FIGS. 1 and 2, an embodiment of the present disclosure provides an electronic cigarette 100. The electronic cigarette 100 includes an atomization module 110, a control module 120, a battery module 130, and a cigarette holder 140. The cigarette holder 140 is detachably mounted on the atomization module 110. The atomization module 110, control module 120, and battery module 130 are detachably and electrically connected to form the electronic cigarette 100. Specially, two of the atomization module 110, the control module 120, and the battery module 130 can be assembled together in connected way or non-connected way, and are both connected to the remaining one of the atomization module 110, the control module 120, and the battery module 130, to form the electronic cigarette 100. For example, as shown in FIG. 3A, the atomization module 110 and the battery module 130 are detachably and electrically connected together, and both of the atomization module 110 and the battery module 130 are detachably and electrically connected to the control module 120. Alternatively, as shown in FIG. 3B, the atomization module 110 and the battery module 130 are non-connected to each other, and both of the atomization module 110 and the battery module 130 are detachably and electrically connected to the control module 120.

The atomization module 110 includes a first magnetic member 111, a second magnetic member 112 and an atomization device 115. The first magnetic member 111 and the second magnetic member 112 are respectively disposed at opposite ends of the atomization device 115. The atomization module 110 further includes a first positive contact 113 and a second positive contact 114 adjacent to the second magnetic member 112 and disposed at one end of the atomization module 110. In the present embodiment, the first positive electrode contact 113 is arranged along a longitudinal axis of the atomization module 110, and the second positive electrode contact 114 is arranged along a horizontal axis of the atomization module 110. Specifically, the first positive electrode contact 113 is arranged at a first end surface 11a of the atomization module 110, and the second positive electrode contact 114 is arranged at a first side surface 11b intersecting the first end surface 11a. The second magnetic member 112 and the first positive electrode contact 113 are spaced apart by an insulating member, to make the first end surface 11a to be a negative electrode, and make the first positive electrode contact 113 to be a positive electrode. The second magnetic member 112 and the second positive electrode contact 114 are also spaced apart by an insulating member, to make the first side surface 11b to be a negative electrode, and make the second positive electrode contact 114 to be a positive electrode.

It can be understood that the first positive electrode contact 113 and the second positive electrode contact 114 may be the same positive electrode contact, and the positive electrode contact is fixed by a rotation shaft. When the electronic cigarette is assembled side by side, the positive electrode contact is turned to the direction of the second positive electrode contact 114; when the electronic cigarette is assembled end to end, the positive electrode contact is turned to the direction of the first positive contact 113.

The control module 120 includes a third magnetic member 121, a fourth magnetic member 122, and a controller assembly 127. The third magnetic member 121 and the fourth magnetic member 122 are respectively arranged at opposite ends of the control module 120, and the controller assembly 127 is arranged between the third magnetic member 121 and the fourth magnetic member 122. The control module 120 further includes a third positive electrode contact 123 corresponding to the first positive electrode contact 113 and a fourth positive electrode contact 124, a fifth positive electrode contact 125 and a sixth positive electrode contact 126 corresponding to the second positive electrode contact 114. The third positive electrode contact 123 is adjacent to the third magnetic member 121 and is arranged at one end of the control module 120. The fourth positive electrode contact 124, the fifth positive electrode contact 125, and the sixth positive electrode contact 126 are arranged at an opposite end of the control module 120. In the present embodiment, the fourth positive electrode contact 124 is arranged along the longitudinal axis of the atomization module 110. The fifth positive electrode contact 125 and the sixth positive electrode contact 126 are both arranged along the horizontal axis of the atomization module 110, but are located at opposite sides of the control module 120. Specifically, the fourth positive electrode contact 124 is arranged at a second end surface 12a of the control module 120. The fifth positive electrode contact 125 is arranged at a second side surface 12b which intersects the second end surface 12a, and the sixth positive electrode contact 126 is arranged at a third side surface 12c which intersects the second end surface 12a and is opposed to the second side surface 12b. The third magnetic member 121 and the third positive electrode contact 123 are spaced apart by an insulating member, to make the third positive electrode contact 123 to be a positive electrode, and make an end surface of the control module 120 where the third positive electrode contact 123 arranged to be a negative electrode. The fourth positive electrode contact 124 and the fourth magnetic member 122 are separated by an insulating member, to make the fourth positive electrode contact 124 to be a positive electrode, and make the second end surface 12a to be a negative electrode. The fifth positive electrode contact 125 and the fourth magnetic member 122 are separated by an insulating member, to make the fifth positive electrode contact 125 to be a positive electrode, and make the second side surface 12b to be a negative electrode. The sixth positive electrode contact 126 and the fourth magnetic member 122 are separated by an insulating member, to make the sixth positive electrode contact 126 to be a positive electrode, and make the third side surface 12c to be a negative electrode.

It can be understood that the fourth positive electrode contact 124 and the fifth positive electrode contact 125 may be the same positive electrode contact, and the positive electrode contact is fixed by a rotation shaft. When the electronic cigarette is assembled side by side, the positive electrode contact is turned to the direction of the fifth positive electrode contact direction 125. When the electronic cigarette is assembled in a end to end manner, the positive electrode contact is turned to the direction of the fourth positive electrode contact 124.

The battery module 130 includes a power supply battery 135, a fifth magnetic member 131, a sixth magnetic member 132, a seventh positive electrode contact 133, and at least one eighth positive electrode contact 134. The fifth magnetic member 131 and the seventh positive electrode contact 133 are arranged at one end of the battery module 130, and the sixth magnetic member 132 and the at least one eighth positive electrode contact 134 are arranged at an opposite end of the battery module 130. The seventh positive electrode contact 133 corresponds to the fourth positive electrode contact 124, and the eighth positive electrode contact 134 corresponds to the fifth positive electrode contact 125. In the present embodiment, the seventh positive electrode contact 133 is arranged along the longitudinal axis of the battery module 130, and the eighth positive electrode contact 134 is arranged along the horizontal axis of the battery module 130.

Specifically, the seventh positive electrode contact 133 is arranged at a third end surface 13a of the battery module 130, and the eighth positive electrode contact 134 is arranged at a fourth side surface 13b intersecting the third end surface 13a. The seventh positive electrode contact 133 and the fifth magnetic member 131 are spaced apart by an insulating member, to make the seventh positive electrode contact 133 to be a positive electrode, and make the third end surface 13a to be a negative electrode. The eighth positive electrode contact 134 and the sixth magnetic member 132 are spaced apart by an insulating member, to make the eighth positive electrode contact 134 to be a positive electrode, and make the fourth side surface 13b to be a negative electrode.

It can be understood that the seventh positive electrode contact 133 and the eighth positive electrode contact 134 may be simultaneously arranged at the same magnetic member (i.e., the fifth magnetic member 131 or the sixth magnetic member 132).

It can be understood, when the seventh positive electrode contact 133 and the eighth positive electrode contact 134 are arranged at the same magnetic member, the seventh positive electrode contact 133 and the eighth positive electrode contact 134 may be the same positive electrode contact, and the positive electrode contact is fixed by a rotation shaft. When the electronic cigarette is assembled side by side, the positive electrode contact is turned to the direction of the eighth positive electrode contact 134. When the electronic cigarette combination is assembled end to end, the positive electrode contact is turned to the direction of the seventh positive electrode contact 133.

It can be understood that a housing of the atomization module 110, a housing of the control module 120, and a housing of the battery module 130 may themselves be magnetic, so that assembly of the atomization module 110, the control module 120 and the battery module 130 may be achieved by the magnetic housings without using the above-described magnetic members.

Figure 5:
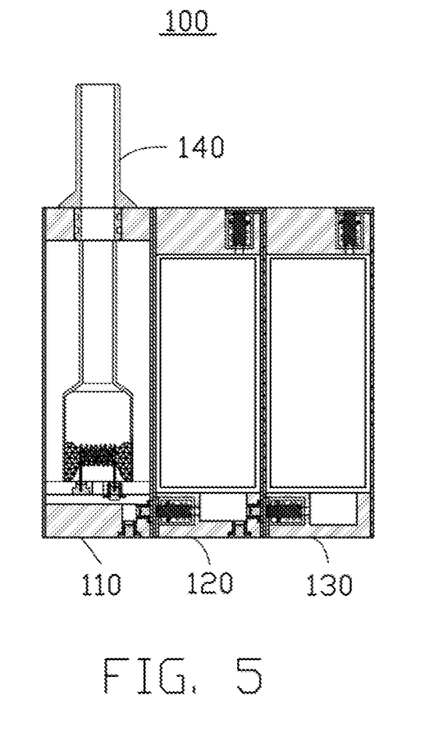
FIG. 5 is a schematic diagram of the electronic cigarette of FIG. 1, showing a side by side assembly type of the electronic cigarette.

The atomization module 110, the control module 120, and the battery module 130 of the electronic cigarette 100 can be assembled in at least two ways. For example, the atomization module 110, the control module 120, and the battery module 130 of the electronic cigarette 100 can be assembled by means of side by side or by means of end to end.

Referring to FIG. 5, the side by side assembly type is that the second positive electrode contact 114 of the atomization module 110 in contact with the sixth positive electrode contact 126 of the control module 120, and the fifth positive electrode contact 125 of the control module 120 in contact with the eighth positive electrode contact 134 of the battery module 130. The atomization module 110, the control module 120, and the battery module 130 are connected by the magnetic members, to make the contacted positive electrode contacts electrically connect to each other. Specifically, the second positive electrode contact 114 and the sixth positive electrode contact 126 are electrically connected, and the fifth positive electrode contact 125 and the eighth positive electrode contact 134 are electrically connected.

Referring again to FIG. 1, the end to end type of assembly is that the first positive electrode contact 113 of the atomization module 110 in contact with the third positive electrode contact 123 of the control module 120, and the fourth positive electrode contact 124 in contact with the seventh positive electrode contact 133.

Figure 4:
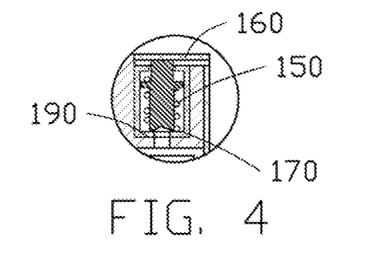
FIG. 4 is an enlarged view of the portion I shown in FIG. 2.

Further, referring to FIG. 4, the third magnetic member 121 defines a mounting hole 190, and the third positive electrode contact 123 is accommodated in the mounting hole 190. The third positive electrode contact 123 includes a sleeve 170, and an elastic member 150 is accommodated in the sleeve 170. The sleeve 170 may be mounted in the mounting hole 190 through tight fit, bonding, and so on. The elastic member 150 is dimensionally tolerant, to allow for small dimensional differences when the electronic cigarette 100 is assembled. In the present embodiment, the sixth positive electrode contact 126, the seventh positive electrode contact 133, and the eighth positive electrode contact 134 have the same structure as the third positive electrode contact 123.

It can be understood that, all the positive electrode contacts on the atomization module 110, the control module 120, and the battery module 130 may be configured to be elastic, and if a dimensional difference occurs when the electronic cigarette 100 is assembled, the elastic contact can effectively resolve the defect.

Figure 6:
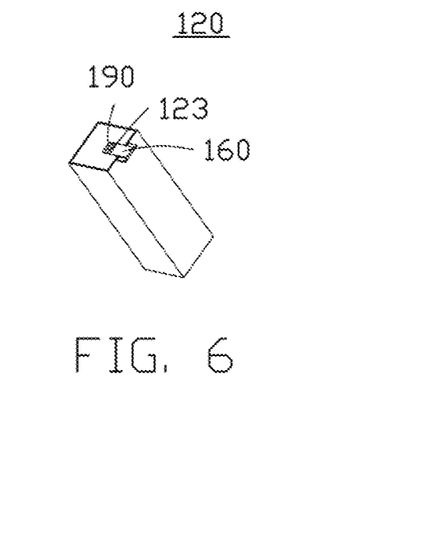
FIG. 6 is a schematic diagram of the ornament of FIG. 2.

Furthermore, referring to FIGS. 2 and 6, the electronic cigarette 100 may further include a plurality of ornaments 160 corresponding to the third positive electrode 123, the sixth positive electrode contact 126, the seventh positive electrode contact 133 and the eighth positive electrode contact 134. In the present embodiment, the ornament 160 to be engaged with the third positive electrode contact 12.3 is illustrated. The mounting hole 190 defines a mounting groove, and the ornament 160 is detachably inserted into the mounting groove. The ornament 160 may also be detachably mounted on the control module 120 in a magnetic manner or in other ways. When the atomization module 110, the control module 120, and the battery module 130 are assembled side by side, the ornament 160 enhances aesthetic appeal by preventing the third positive electrode contact 123 from being exposed.

In other embodiments, the control module 120 may be omitted according to actual production requirements. The electronic cigarette 100 includes the atomization module 110 and the battery module 130 which is directly and electrically connected to the atomization module 110, that is, the battery module 130 directly supplies power to the atomization module 110.

In other embodiments, the electronic cigarette 100 is not limited to including one atomization module 110 and one battery module 130, the electronic cigarette 100 may include two or more than two battery modules 130. The connections between the two or more than two battery modules 130 are the same as the connections between the battery module 130 and the control module 120 described above. In this way, the two or more than two battery modules 130 can be used simultaneously to extend a power supply time of the electronic cigarette 100, and a spare battery module 130 may be added to increase the power supply when one battery module 130 does not have enough power.

In other embodiments, the positive electrode contacts which are at each of the modules may be replaced by other forms of electrical connections depending on actual production requirements.

The Second Embodiment

Figure 7A:
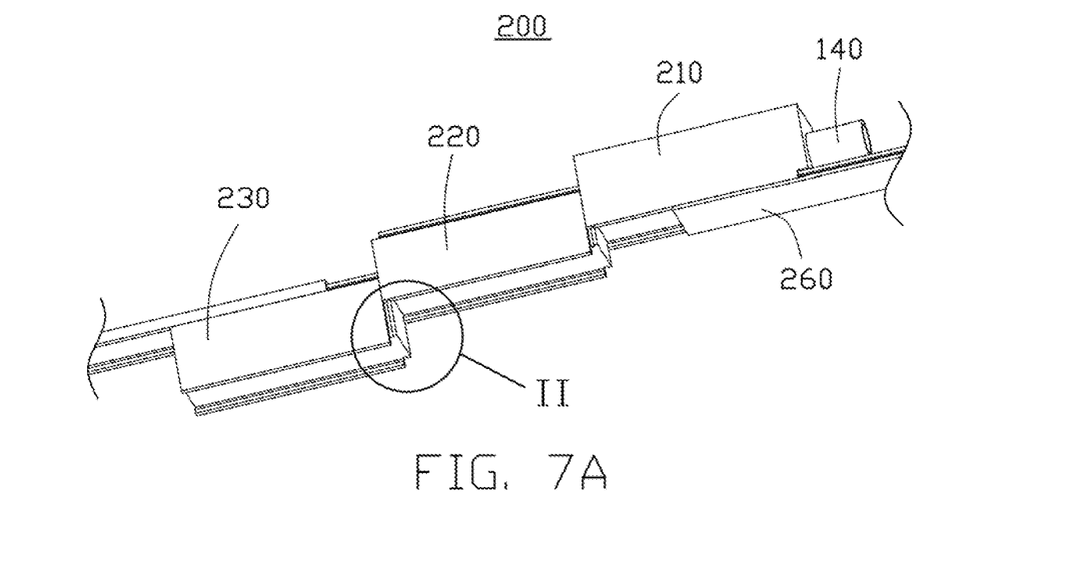
FIG. 7A is a schematic diagram of a snap-fit connection of an electronic cigarette according to another embodiment of the present disclosure, wherein the electronic cigarette is assembled end to end.
Figure 7B:
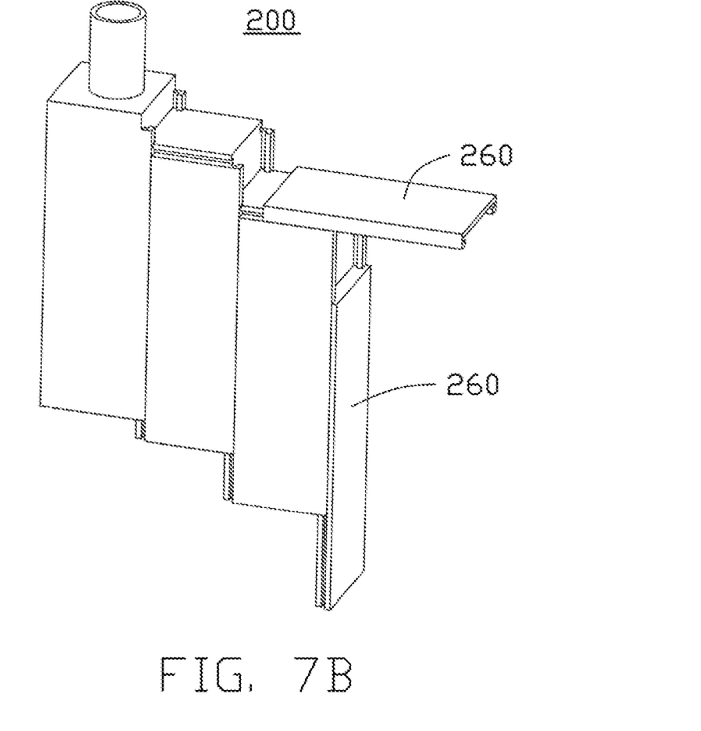
FIG. 7B is a schematic diagram of a snap-fit connection of an electronic cigarette according to another embodiment of the present disclosure, wherein the electronic cigarette is assembled side by side.
Figure 8:
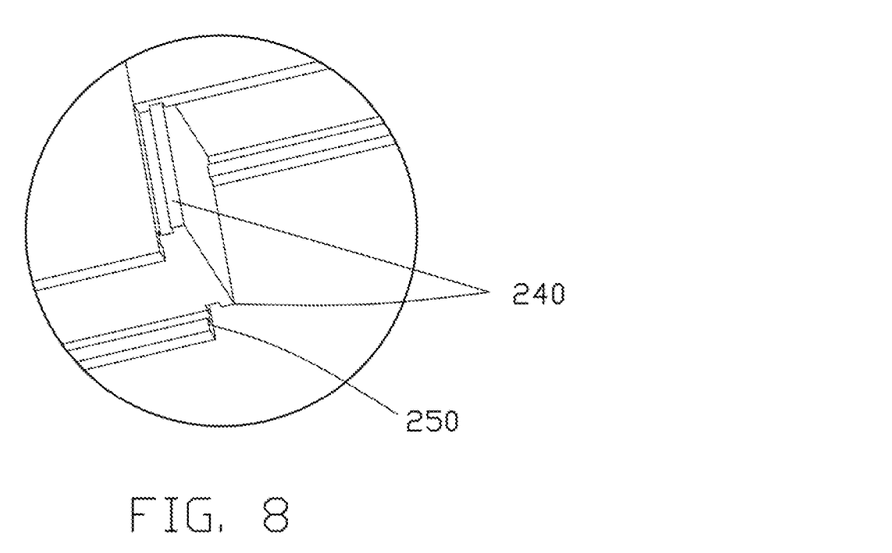
FIG. 8 is an enlarged view of the portion II of FIG. 7A.

Referring to FIGS. 7A and 7B, the present disclosure also provides an electronic cigarette 200 of another embodiment. The electronic cigarette 200 includes an atomization module 210, a control module 220, and a battery module 230 which are detachably and electrically connected together in a snap-fit manner. The atomization module 210, control module 220, and battery module 230 can be freely combined. One end surface of the battery module 230 is provided with a T-shaped joint 240, and the other end surface defines a connection groove 250 opposite to the joint 240.

Further, one side surface adjacent to the two end surfaces of the battery module 230 is provided with a joint 240, and the other side surface opposite to the side surface defines a connection groove 250.

It can be understood that the control module 220 and the atomization module 210 are both provided with joints 240 and connection grooves 250, and the arrangements of the joints 240 and the connection grooves 250 on the control module 220 and the atomization module 210 are similar to the arrangements of the joints 240 and the connection grooves 250 on the battery module 230.

The connection manner of this embodiment is that when the electronic cigarette 200 is assembled end to end, the joint 240 of the end surface of the battery module 230 is engaged with the connection groove 250 of the end surface of the control module 220, and the joint 240 of the end surface of the control module 220 is engaged with the connection groove 250 of the end surface of the atomization module 210. Similarly, when the electronic cigarette is assembled side by side, the joint 240 of the side surface of one module is engaged with the connection groove 250 of the side surface of another module.

Further, the electronic cigarette 200 further includes a plurality of ornament plates 260 corresponding to different joints 240 or connecting grooves 250, and having different lengths to improve outward appearance of the electronic cigarette 200.

It can be understood that the atomization module 210 may only include the joints 240 or the connecting grooves 250 as connecting members, the connecting members of the control module 220 and the battery module 230 may be adjusted in accordance with the connecting members of the atomization module 210.

It can be understood that the shape and structure of the joints 240 and the connection grooves 250 can be changed according to actual production requirements, to ensure that the atomization module 210, the control module 220 and the battery module 230 can be detachably and freely combined together.

The Third Embodiment

Figure 9A:
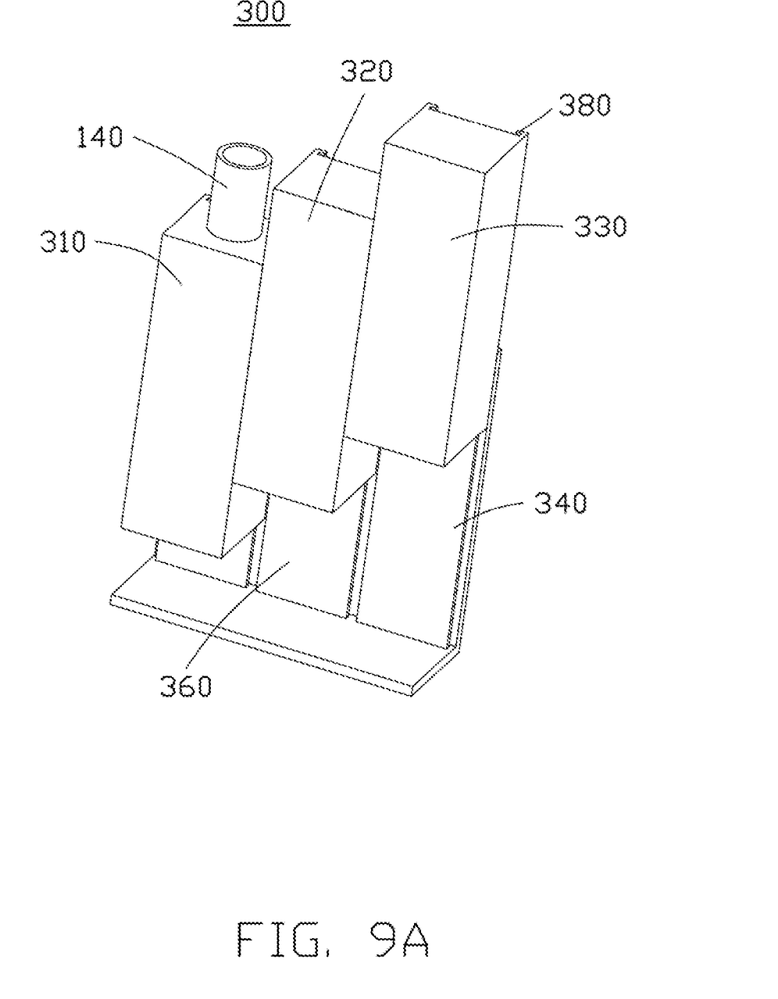
FIG. 9A is a schematic illustration diagram of an auxiliary assembly of an electronic cigarette according to another embodiment of the present disclosure, wherein the electronic cigarette is assembled end to end.
Figure 9B:
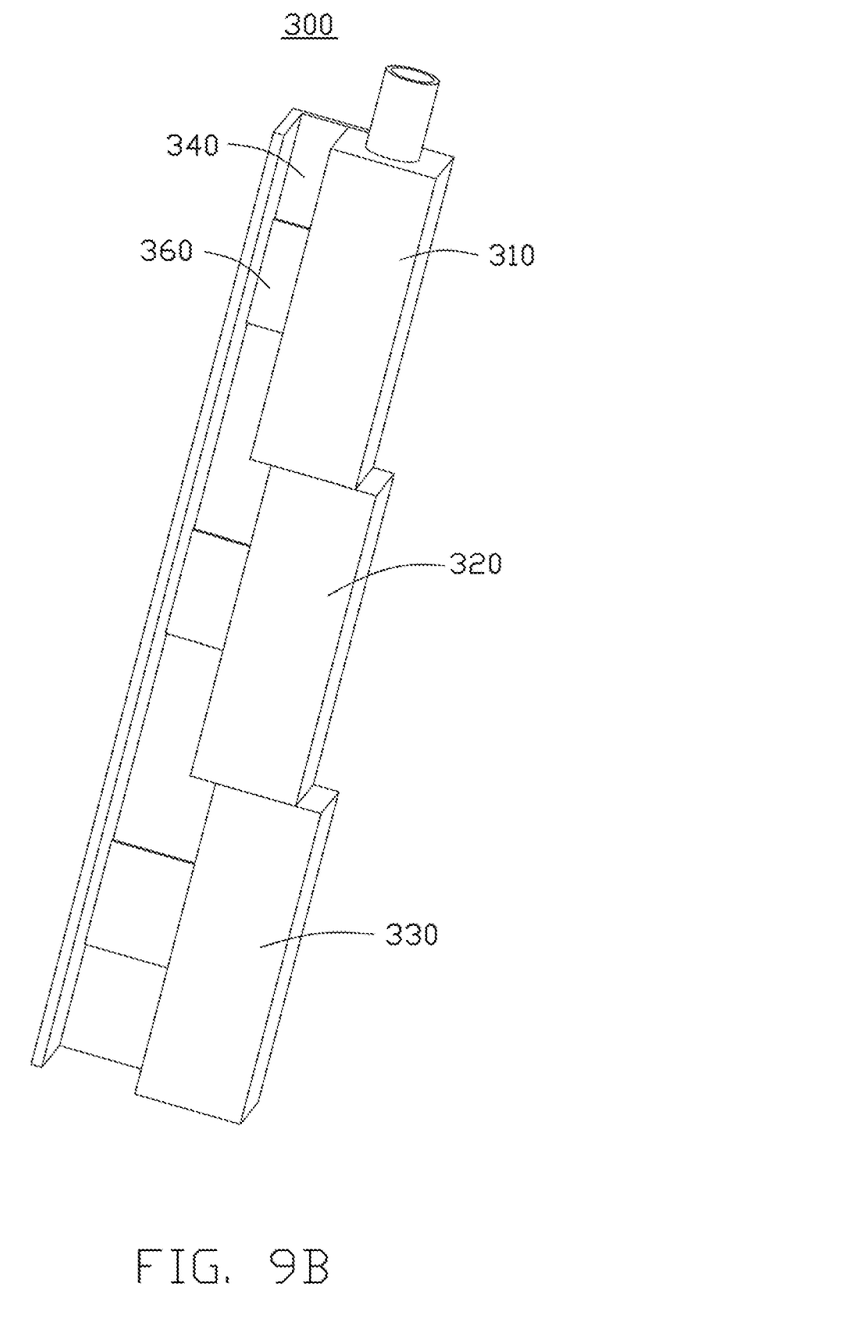
FIG. 9B is a schematic illustration diagram of an auxiliary assembly of an electronic cigarette according another embodiment of the present disclosure, wherein the electronic cigarette is assembled side by side.

Referring to FIGS. 9A and 9B, an electronic cigarette 300 according to another embodiment of the present disclosure includes an atomization module 310, a control module 320, a battery module 330, and at least one accessory 340. The accessory 340 includes a plurality of T-shaped locking portions 360, and one side surface of each module defines a slot 380 corresponding to a locking portion 360. The modules can be detachably attached to the accessory 340 to assemble the electronic cigarette 300 into a specific shape through the plurality of the locking portions 360 engaging with the slots 380. In other embodiments, the locking portions 360 may be formed on the modules, and the slots 380 may be defined on the accessory 340 at the same time.

it can be understood that the shape of the accessory 340 can be different depending on the combination shape of the electronic cigarette 300. Thus, different combination shapes of the electronic cigarette 300 need to select the accessory 340 which has corresponding shapes and configurations.

In other embodiments, the locking portions 360 are not limited to the T-shaped structure, and the locking portions 360 may be in other configurations and shapes as long as the locking portions 360 matching with the slots 380.

in other embodiments, the slots 380 may be provided on the accessory 340, and the locking portions 360 are defined on the atomization module 310, the control module 320, and the battery module 330.

In other embodiments, the assembly of the atomization module 310, the control module 320, the battery module 330, and the accessory 340 may be performed by a connection other than the snap-fit, such as a magnetic connection, a threaded connection, or other connection ways.

In other embodiments, the atomization module 310, the control module 320, and the battery module 330 may also be detachably assembled by means of using USB plug and USB socket.

It can be understood that in the second, third, or other embodiments of the present disclosure, the electronic cigarette may include at least two battery modules, so that the at least two battery modules can be used simultaneously to extend the power supply time of the electronic cigarette, and a spare battery module may be added to increase the power supply when one battery module does not have enough power.

It can be understood that when the electronic cigarette does not include a control module, the atomization module and the battery module can be detachably and freely connected in any one of the above-described connection ways.

It can be understood that the component combination of the electronic cigarette is not limited to end to end and side by side manner, and on the basis of the structure and shape of each module, the electronic cigarette can be assembled into an arc shape, V-shape, or triangle shape to meet different needs of the user.

The above-described embodiments express only the embodiments of the present disclosure, which are more specific and detailed, but are not to be construed as limiting the scope of the invention. It should be noted that various modifications and improvements can be made by those skilled in the art without departing from the spirit of the invention, which are within the scope of the present invention. Accordingly, the scope of protection of the present disclosure should be determined by the appended claims.

What is claimed is:

1. An electronic cigarette comprising:
at least one atomization module;
at least one battery module; and
a control module;
wherein each atomization module, each battery module and the control module comprise at least two magnetic members, end surfaces of each atomization module, each battery module and the control module comprise at least one magnetic member, side surfaces of each atomization module, each battery module and the control module are provided with at least one of the magnetic member;
the at least one atomization module, the at least one battery module, and the control module are assembled by the magnetic members in two ways to obtain the electronic cigarette in a side-by-side configuration and an end-to-end configuration.

2. The electronic cigarette as claim 1, wherein a housing of each atomization module and a housing of each battery module are both magnetic housings.

3. The electronic cigarette as claim 1, wherein the electronic cigarette further comprises at least one ornament, the at least one magnetic member defines a mounting hole in which an electrical connection is accommodated, and the mounting hole defines a mounting groove for detachably assembling one ornament.

4. The electronic cigarette as claim 1, wherein at least one surface of each atomization module and at least one surface of each battery module are both provided with a joint or a connection groove, and the at least one atomization module and the at least one battery module are detachably connected together by means of snap-fit manner.

5. The electronic cigarette as claim 1, wherein at least one surface of each atomization module, at least one surface of each battery module and at least one surface of the control module are all provided with a joint or a connection groove, and the at least one atomization module, the at least one battery, and the control module are detachably connected together by means of snap-fit manner.

6. The electronic cigarette as claim 1, wherein the electronic cigarette comprises an accessory, the at least one atomization module and the at least one battery module are detachably mounted on the accessory by magnetic attraction or snap-fit engagement.

7. The electronic cigarette as claim 1, wherein the electronic cigarette comprises an accessory, the at least one atomization module, the at least one battery module and the control module are detachably mounted on the accessory by magnetic attraction or snap-fit engagement.

8. The electronic cigarette as claim 6, wherein the accessory comprises a plurality of joints or connection slots, each atomization module and each battery module are both provided with a connection slot or a joint, and each atomization module and each battery module are slidably mounted to the accessory.

9. The electronic cigarette as claim 8, wherein a configuration and/or shape of the accessory is selected depending on a combination type of the electronic cigarette.

10. The electronic cigarette as claim 1, wherein the number of the at least one battery module is two or more than two.

11. The electronic cigarette as claim 1, wherein:
both the number of the atomization module and the number of the battery module are one,
the atomization module comprises an atomization device and two magnetic members,
one of the two magnetic members of the atomization module is positioned at an end surface of the atomization device, and the other of the two magnetic members of the atomization module is positioned at a side surface of the atomization device,
the battery module comprises a power supply battery and four magnetic members,
two magnetic members of the battery module are positioned at two opposite end surfaces of the power supply battery, and the other two magnetic members of the battery module are positioned at two site side surfaces of the power supply battery,
the control module comprises a controller assembly and two magnetic members,
one of the two magnetic members of the control module is positioned at an end surface of the controller assembly, and the other of the two magnetic members of the control module is positioned at a side surface of the controller assembly, the magnetic members are connected in two ways by magnetic attraction to obtain the electronic cigarette in the side-by-side configuration and the end-to-end configuration.

* * * * *